United States Patent
Niu et al.

(10) Patent No.: US 9,241,678 B2
(45) Date of Patent: Jan. 26, 2016

(54) RANDOM ESTIMATION IN POSITRON EMISSION TOMOGRAPHY WITH TANGENTIAL TIME-OF-FLIGHT MASK

(75) Inventors: Xiaofeng Niu, Mundelein, IL (US); Wenli Wang, Briarcliff Manor, NY (US)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 13/467,090

(22) Filed: May 9, 2012

(65) Prior Publication Data
US 2013/0304386 A1    Nov. 14, 2013

(51) Int. Cl.
| | |
|---|---|
| G01N 33/48 | (2006.01) |
| G01N 33/50 | (2006.01) |
| G01N 31/00 | (2006.01) |
| G06G 7/48 | (2006.01) |
| A61B 6/03 | (2006.01) |
| G06F 19/22 | (2011.01) |
| G06F 19/24 | (2011.01) |
| G06F 19/12 | (2011.01) |

(52) U.S. Cl.
CPC ............... *A61B 6/037* (2013.01); *G06F 19/12* (2013.01); *G06F 19/22* (2013.01); *G06F 19/24* (2013.01)

(58) Field of Classification Search
None
See application file for complete search history.

(56) References Cited

U.S. PATENT DOCUMENTS

| | | | |
|---|---|---|---|
| 7,414,246 B2 * | 8/2008 | Griesmer et al. | 250/363.09 |
| 2005/0129170 A1 * | 6/2005 | Watson et al. | 378/5 |
| 2008/0317194 A1 | 12/2008 | Gagnon et al. | |
| 2010/0072375 A1 | 3/2010 | Panin | |
| 2013/0009064 A1 | 1/2013 | Yoshida et al. | |

FOREIGN PATENT DOCUMENTS

| | | |
|---|---|---|
| JP | 7-113873 A | 5/1995 |
| JP | 09-184885 | 7/1997 |
| JP | 2007-71858 A | 3/2007 |
| WO | WO 2011/117990 A1 | 9/2011 |

OTHER PUBLICATIONS

Wang et al. 4-D Geometric sensitivity for multi-headed planar detector PET systems. IEEE Nuclear Science Symposium and Medical Imaging Conference, 2001, pp. 1104-1108.*
Wang et al. Noise analysis of MAP-EM algorithms for emission tomography. Physics in Medicine and Biology, vol. 42, 1997, pp. 2215-2232.*
Kao et al. Evaluation of 3D image reconstruction methods for a dual-head small-animal PET scanner. IEEE Nuclear Science Synposium Conference Record, 2007, pp. 2864-2868.*
Kao et al. An investigation of the potential benefits in trading energy resolution for timing resolution in time-of-flight positron emission tomography. 2006 IEEE Nuclear Science Symposium Conference Record, pp. 2564-2569.*

* cited by examiner

*Primary Examiner* — Russell S Negin
(74) *Attorney, Agent, or Firm* — Oblon, McClelland, Maier & Neustadt, L.L.P.

(57) ABSTRACT

A method of estimating random events in positron emission tomography list mode data, including obtaining time-of-flight (TOF) list mode count data that includes TOF information; converting the obtained TOF list mode count data into four-dimensional (4D) raw sinogram count data, without using the TOF information, wherein the 4D raw sinogram count data includes random count values; interpolating the 4D raw sinogram count data to generate 4D interpolated sinogram count data; low-pass filtering the 4D interpolated sinogram count data to remove noise; converting the low-pass filtered 4D interpolated sinogram count data into filtered 4D raw sinogram count data; and generating, by a processor, five-dimensional (5D) TOF raw sinogram count data from the filtered 4D raw sinogram count data by effectively applying a TOF mask filter to the filtered 4D raw sinogram count data.

8 Claims, 6 Drawing Sheets

RANDOM ESTIMATION IN POSITRON EMISSION TOMOGRAPHY WITH TANGENTIAL TIME-OF-FLIGHT MASK

FIELD

Embodiments described herein relate generally to random event estimation in time-of-flight data acquired in a gamma ray detection system.

BACKGROUND

Positron emission tomography (PET) is a branch of nuclear medicine in which a positron-emitting radiopharmaceutical is introduced into the body of a patient. As the radiopharmaceutical decays, positrons are generated. More specifically, each of a plurality of positrons reacts with an electron in what is known as a positron annihilation event, thereby generating a coincident pair of gamma photons which travel substantially in opposite directions along a line of coincidence. A gamma photon pair detected within a coincidence time is ordinarily recorded by the PET scanner as an annihilation event.

In time-of-flight ("TOF") imaging, the time within the coincidence interval at which each gamma photon in the coincident pair is detected is also measured. The time of flight information provides an indication of the location of the detected event along the line of coincidence. Data from a plurality of annihilation events is used to reconstruct or create images of the patient or object scanned, typically by using statistical (iterative) or analytical reconstruction algorithms.

FIG. 1 illustrates the transaxial and axial coordinates of an emitted positron and the measured line of response (LOR) of a 3D detector. The coordinates $(x_e, y_e, z_e)$ or $(s_e, t_e, z_e)$ define the emitted positron's image coordinate. The measured LOR's projection coordinate can be defined by either $(s, \phi, z, \theta)$, where $z=(z_a+z_b)/2$, or may include the additional dimension t for a TOF-LOR.

In PET, random coincidences occur due to the finite width of the coincidence window, which is used to detect true coincidences. If two uncorrelated single events are detected within the coincidence window, they can mistakenly be identified as a true coincidence event and recorded. The rate of random events is proportional to the single event rate on each detector and the size of coincidence window, as shown in Equation (1):

$$C_{ij} = 2\tau r_i r_j \quad (1)$$

in which $C_{ij}$ represents the random coincidences count rate on the LOR that connects the i-th and j-th detectors, $r_i$, $r_j$ represents the single count event rates of the i-th and j-th detectors, and $\tau$ is the coincidence window size.

Random coincidences can comprise a large portion of the recorded prompt coincidence events (which include true, scatter, and random coincidence events), especially in the operation of a 3D PET scanner and high radioactivity concentration. If not compensated for properly, random coincidence events can introduce substantial quantitative errors in the reconstructed images.

The most accurate and commonly used method for random estimation involves the use of a delayed coincidence window. The delayed coincidence window can remove the correlation of two single events in each recorded pair event. Since the delayed coincidence window is usually postponed several ten-to-hundred times the coincidence window size, the possibility of two recorded single events being from a single annihilation is very rare. Therefore, in this method, only random events are recorded.

Recently, a time-of-flight mask was designed to reduce random events in the prompt data by completely filtering out those random coincidences that provide no contribution to the reconstruction field-of-view (FOV). In this process, random events with a TOF difference out of the mask will be removed before reconstruction starts, which leads to more accurate reconstructed images in list-mode reconstruction and lower computation time.

In TOF list-mode reconstruction, the random events with TOF information are estimated in the following way. The non-TOF delay list-mode data are first rebinned and interpolated to a 4D interp-sinogram, smoothed, and then back-interpolated to a 4D raw-sinogram. In the last step, a 5D TOF raw-sinogram is generated by spreading the LOR counts evenly into tangential t-bins, and considering the difference in t-ranges along the LOR's radial direction and oblique angle.

However, with the TOF mask applied, the random distribution will be changed with the introduced circular-edged TOF mask, which causes more random events collected in the central regions of field-of-view (FOV) and fewer random events collected at the edges of FOV. The previously described procedure without TOF mask is not applicable in this case. The reasons are (1) the random smoothing step will change the random distribution over the s dimension, which may bring in estimation error during the back-interpolation step, and (2) when spreading the LOR counts evenly into each tangential t-bin, it is assumed that the random events counts are uniformly distributed along the t dimension, which is not true after applying the TOF mask. Thus, the random events are collected more in the center of the FOV, but fewer are collected at the circular edges of the TOF mask.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

Figure 1:
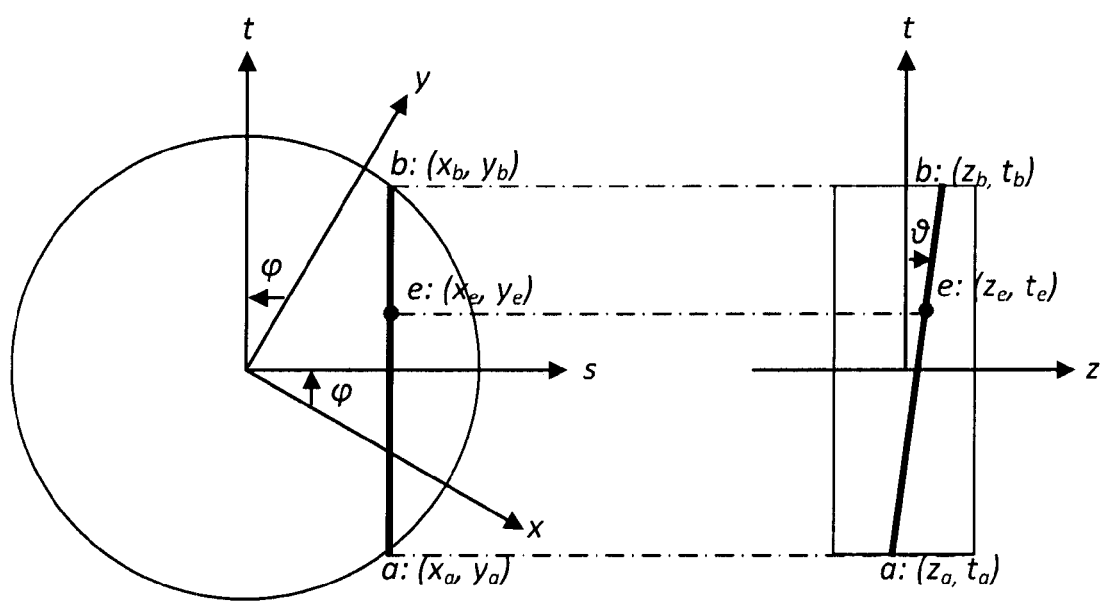
FIG. 1 illustrates an example of a geometry of a PET imaging apparatus.

According to one embodiment, there is provided a method of estimating random events in positron emission tomography list mode data, the method comprising: (1) obtaining time-of-flight (TOF) list mode count data that includes TOF information; (2) converting the obtained TOF list mode count data into four-dimensional (4D) raw sinogram count data, without using the TOF information, wherein the 4D raw sinogram count data includes random count values; (3) interpolating the 4D raw sinogram count data to generate 4D interpolated sinogram count data; (4) low-pass filtering the 4D interpolated sinogram count data to remove noise; (5)

converting the low-pass filtered 4D interpolated sinogram count data into filtered 4D raw sinogram count data; and (6) generating, by a processor, five-dimensional (5D) TOF raw sinogram count data from the filtered 4D raw sinogram count data by effectively applying a TOF mask filter to the filtered 4D raw sinogram count data.

In another embodiment, the generating step includes generating the 5D TOF raw sinogram count data r̂(rad, phi, slice, t) at each TOF bin t according to the following equation:

$$\hat{r}(rad, phi, \text{slice}, t) = \frac{t\_binsz}{t_{coin}\cos\theta} r(rad, phi, \text{slice})$$

wherein $r_{coin}$ is a size of a coincidence window in mm, tof$_{binsz}$ is a TOF bin size in mm, r(rad, phi, slice) is filtered 4D raw sinogram random count data, (rad,phi,slice) are coordinates of a line-of-response (LOR) in the raw sinogram space, and $\theta$ is an oblique angle of the LOR.

According to another embodiment, the obtaining step includes obtaining the TOF list mode data, which for each coincident event, has a format $\{x_a, z_a, x_b, z_b, e_a, e_b, \text{tof}\}$, wherein $x_a$, $x_b$ are incident transverse crystal numbers of events a and b, respectively; $z_a$, $z_b$ are incident axial crystal numbers of events a and b; and $e_a$, $e_b$ are energy levels of events a and b, respectively, and tof is an arrival time difference of events a and b.

In another embodiment, the method includes estimating the random count values within the 4D raw sinogram count data using a delayed coincidence window method.

Non-TOF list mode data generally has the following format for each coincident event: $\{x_a, z_a, x_b, z_b, e_a, e_b\}$ wherein $x_a$, $x_b$ are the incident transverse crystal numbers of events a and b, respectively; $z_a$, $z_b$ are the incident axial crystal numbers of events a and b, respectively; and $e_a$, $e_b$ are the energy levels of events a and b, respectively. Similarly, TOF list mode data has the format $\{x_a, z_a, x_b, z_b, e_a, e_b, \text{tof}\}$, wherein tof is the arrival time difference of events a and b.

Random estimation in TOF list-mode reconstruction by using the delayed coincidence window method can be performed using a 5D or a 4D approach. The 5D method includes the following steps:

(1) the TOF delay window list-mode data is rebinned into 5D raw-sinogram (rad,phi,slice,t) data;

(2) forward interpolation is performed to convert the LOR sinogram (rad,phi,slice,t) data into interpolated, uniform sinogram (s,φ,zθ,t) data;

(3) a sinogram-based 5D low-pass filter is used to reduce the variance of the random data; and (4) the random estimation is obtained by back-interpolation to convert the interpolated uniform sinogram (s,φ,z,θ,t) data back into LOR sinogram (rad,phi,slice,t) data.

Similarly, the 4D method includes the following steps:

(1) the TOF delay window list-mode data is rebinned into 4D raw sinogram (rad,phi,slice) data;

(2) forward interpolation is performed to convert the LOR sinogram (rad,phi,slice) data into interpolated uniform sinogram (s,φ,z,θ) data;

(3) a sinogram-based 4D low-pass filter is used to reduce the variance of the random data;

(4) back interpolation is used to convert the interpolated uniform sinogram (s,φ,z,θ) data back into LOR sinogram (rad,phi,slice) data; and (5) the back-interpolated events are evenly divided into tangential t-bins at (rad,phi,slice) along the t-dimension to generate the random estimation at (rad,phi,slice,t).

Figure 2:
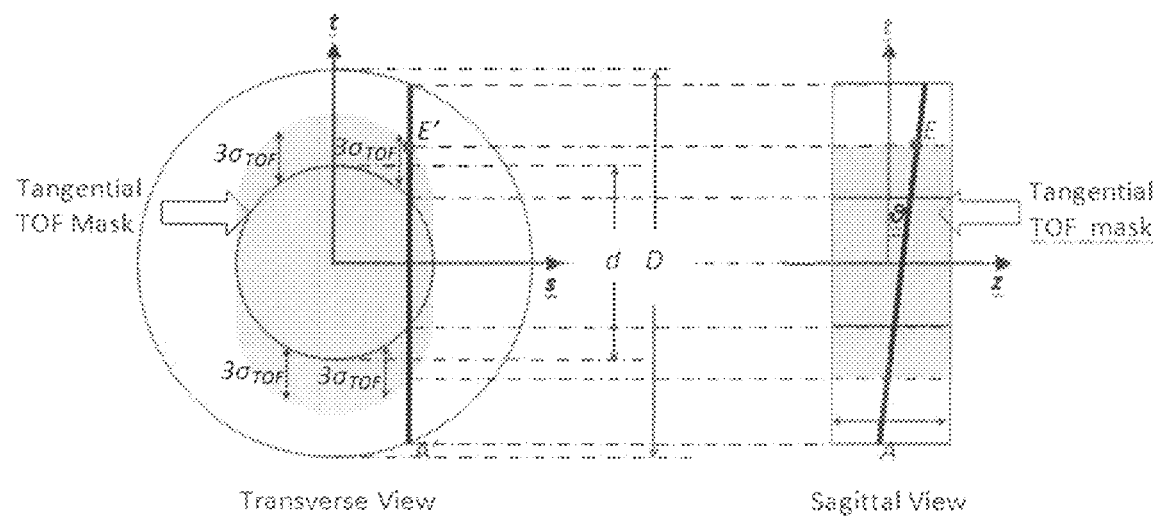
FIG. 2 illustrates a novel TOF mask in both transverse and sagittal views.

However, the above methods can not be used with the novel time-of-flight mask disclosed by the present embodiments. In particular, the random distribution will be changed with the circular-edged TOF mask shown in FIG. 2. As shown in FIG. 2, the TOF mask shape is related to the radial distances as in Equation (2) below.

$$t_{range}(s) = 2\left(\sqrt{\frac{d^2}{4} - s^2} + 3\sigma_{TOF}\right)(mm) \quad (2)$$

Since the random distribution tends to be slow-changing and nearly uniform across the FOV, the distribution of randoms will be different after the TOF mask is applied. Thus, a new random correction method is needed in accordance with the novel TOF mask.

As shown in FIG. 2, there are more zero t bins at large radial positions(s). So, in the last step of the methods shown above, the random counts can not be distributed uniformly along the t-dimension. The shape of the TOF mask needs to be taken into consideration.

Accordingly, in the disclosed embodiments, a new method for random estimation of each event in TOF list-mode reconstruction with a TOF mask applied is used. Instead of using the TOF-mask-filtered random list-mode data, the inventive embodiments use the random list-mode data without TOF mask, which we refer as the original random data.

Figure 3A:
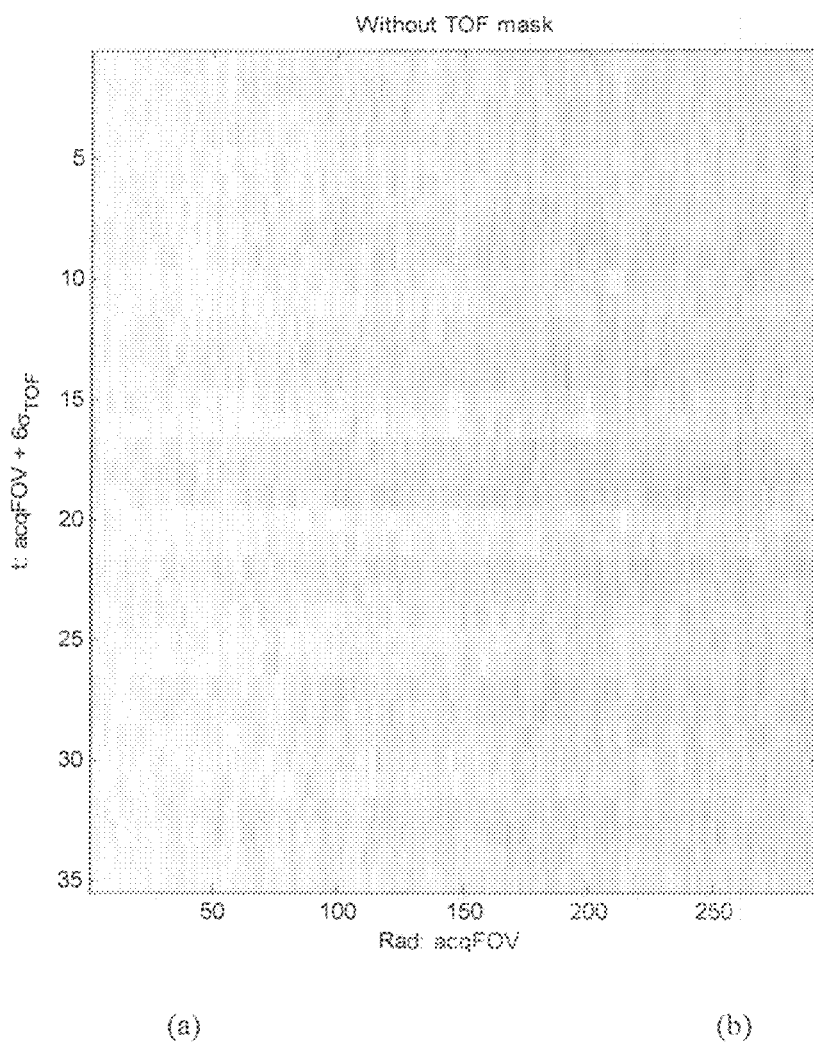
FIG. 3A illustrates the (rad,t) view of 5D random raw-sinogram simulated GATE IEC phantom data with 600 mm FOV without TOF mask.

The original random data distribution (before applying the TOF mask filter) is independent of the TOF dimension, and thus uniform along the tangential t-dimension. As shown in FIG. 3A, the random distribution is nearly uniform along the t-dimension for each radial distances, except for the statistical uncertainty. After filtered with the TOF mask, the random distribution is still uniform along the t-dimension within the TOF mask, but its range varies along the LOR's radial direction, as indicated by s-coordinate in FIG. 2.

Figure 3B:
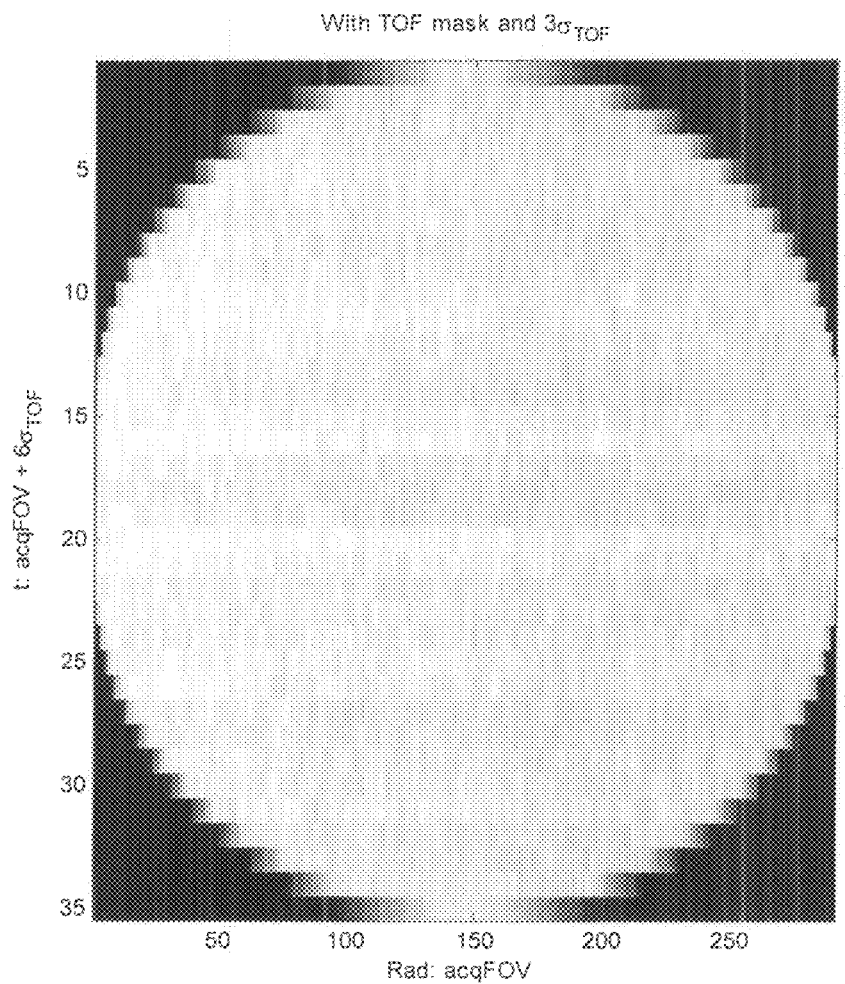
FIG. 3B illustrates the (rad,t) view of 5D random raw-sinogram simulated GATE IEC phantom data with 600 mm FOV with TOF mask and $3\sigma_{TOF}$.

As shown in FIG. 3B, there are more nonzero t-bins at the radial center than at the edges. Further, the range of random distribution along the t-dimension decreases with increasing tilt angle $\theta$ of the LOR. The present inventors have discovered that the random distribution is exactly the same in the region covered by the inventive TOF mask, with or without the TOF mask applied.

Figure 4:
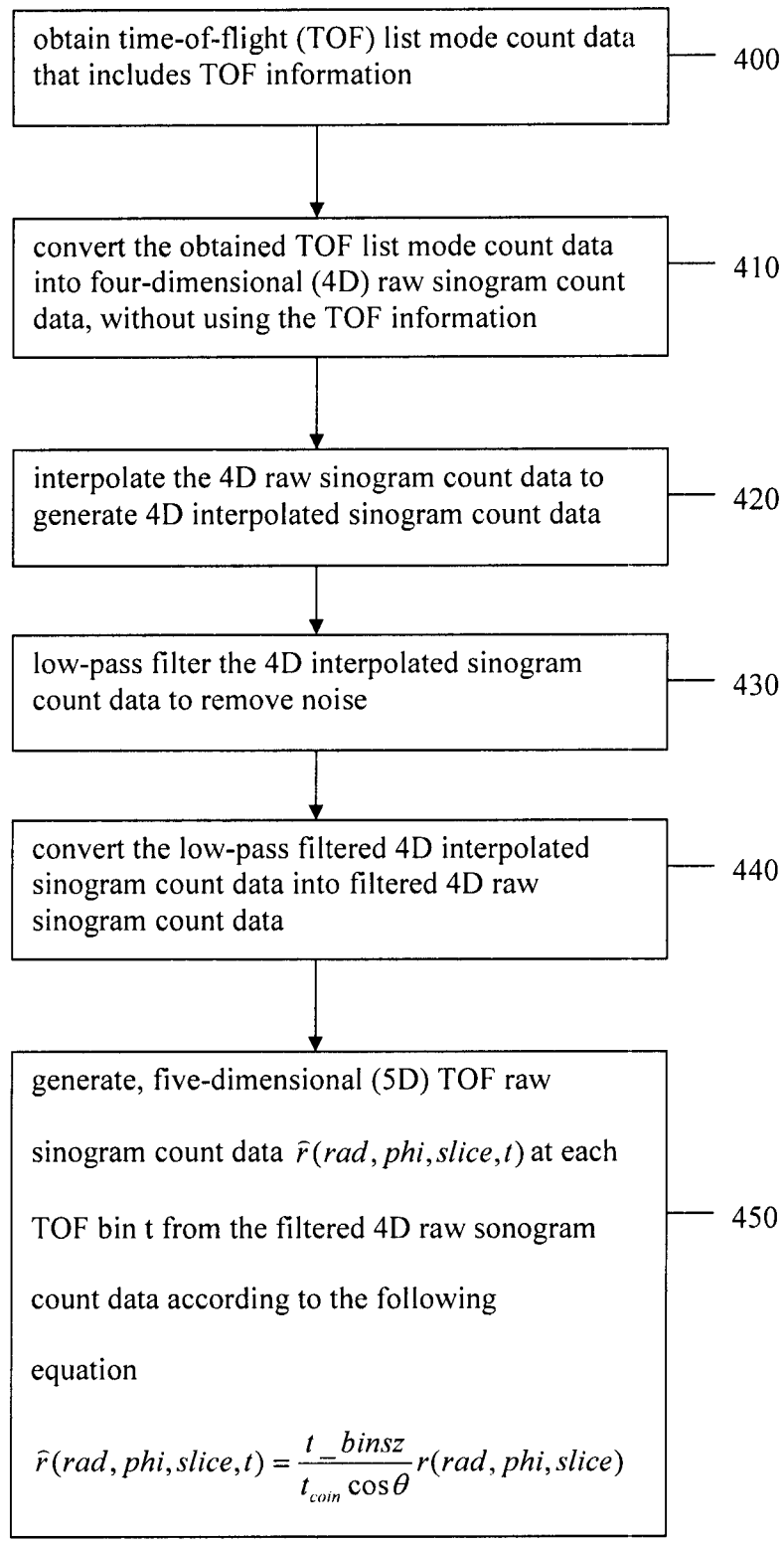
FIG. 4 is a flowchart of a method of estimating random events in PET according to one embodiment.

Based on this discovery, a novel random estimation procedure for TOF list-mode reconstruction with the TOF mask applied is disclosed below. In particular, in one embodiment, the random estimation process is as shown in FIG. 4.

In step 400, time-of-flight (TOF) list mode count data that includes TOF information is obtained. As discussed above, TOF list mode data has the format $\{x_a, z_a, x_b, z_b, e_a, e_b, \text{tof}\}$, wherein tof is the arrival time difference of events a and b.

In step 410, the non-TOF delay list-mode data (without TOF mask filter) are first rebinned into a (rad,phi,slice) raw sinogram. In this step, the TOF portion of the data is ignored.

In step 420, the (rad,phi,slice) raw sinogram data is interpolated into 4D interpolated sinogram (s,φ,z,θ) data.

In step 430, a sinogram-based low-pass smoothing process is applied to remove the statistical noise in the data.

In step 440, the smoothed sinogram (s,φ,zθ) data is back-interpolated to 4D (rad,phi,slice) raw-sinogram data r.

In step 450, 5D TOF raw-sinogram data r̂(rad,phi,slice,t) is generated by spreading the LOR counts evenly into each of the tangential t-bins, and considering the difference in t-ranges along the LOR's radial direction and oblique angle $\theta$. In particular, the estimated random count in each t-bin is determined by Equation (3) below:

$$\hat{r}(rad, phi, \text{slice}, t) = \quad (3)$$

$$\frac{t_{range}(s)}{t_{coin}\cos\theta} \frac{t_{binsz}}{t_{range}(s)} r(rad, phi, \text{slice}) = \frac{t_{binsz}}{t_{coin}\cos\theta} r(rad, phi, \text{slice})$$

with $t_{coin}$ representing the size of coincidence window in mm, $t_{binsz}$ representing the t bin size in mm, and $t_{range}(s)$ is defined as in Eqn. (2), representing the t-ranges at each s. Note that the 5D TOF raw-sinogram $\hat{r}(rad, phi, \text{slice}, t)$ generated by Eqn. (3) has the effect of applying the TOF mask shown in FIG. 2.

For example, if a ±4.2 ns coincidence window is used, $t_{coin}=2*4200*0.15=1260$ mm, and if $t_{binsz}=20$ mm and $\theta=0$, then each r(rad, phi, slice) is scaled by 0.0159 to get $\hat{r}$(rad, phi, slice, t). Thus, Eqn. 3 is used to estimate the effect of applying the TOF mask, without actually filtering the data with the TOF mask.

In an alternative embodiment, step 410 and/or step 440 can be omitted. For example, after step 400, step 420 can be performed so that 4D interpolated sonogram data is obtained directly from the list mode data.

Moreover, the novel random estimation method with TOF mask can also be applied in sinogram-based image reconstruction, rather than list-mode reconstruction. In this case, the reconstruction engine can use the TOF information or not. When using the TOF information in reconstruction, the estimated randoms will be in a 5D TOF interpolated-sinogram. When not using the TOF information in reconstruction, the TOF mask can still be used to reject some of the random counts, but the reconstruction engine itself does not use the TOF information, so that a 4D non-TOF interpolated-sinogram is used.

The novel random estimation method for TOF list-mode reconstruction described above has several advantages. In particular, based on the uniformity of random event distribution along the t-dimension, the random events in the prompt data can be estimated by using the non-TOF delay list-mode data without a TOF mask filter. The benefit of using the TOF mask during the reconstruction is still valid. Moreover, there is no increased complexity of random correction with the novel TOF mask shape. As shown in Eqn. (3), the scale factor $$\frac{t_{binsz}}{t_{coin}\cos\theta}$$

of estimated random counts are independent of the radial distances.

Figure 5:
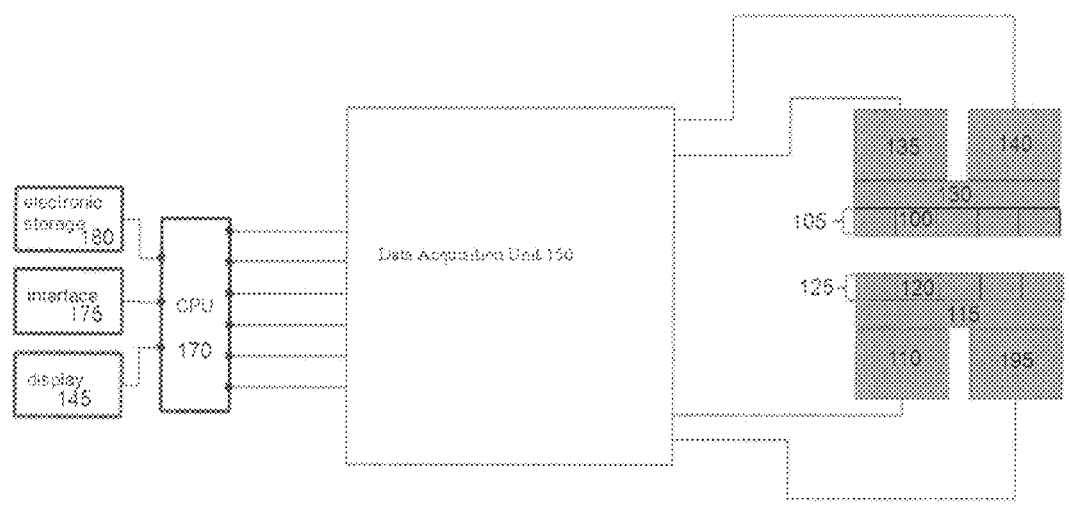
FIG. 5 illustrates PET system hardware according to one embodiment.

FIG. 5 shows an exemplary PET hardware configuration that can be used with the present embodiments. In FIG. 5, photomultiplier tubes 135 and 140 are arranged over light guide 130, and the array of scintillation crystals 105 is arranged beneath the light guide 130. A second array of scintillation crystals 125 is disposed opposite the scintillation crystals 105 with light guide 115 and photomultiplier tubes 195 and 110 arranged thereover.

In FIG. 5, when gamma rays are emitted from a body under test, the gamma rays travel in opposite directions, approximately 180° from each other. Gamma ray detection occurs simultaneously at scintillation crystals 100 and 120, and a scintillation event is determined when the gamma rays are detected at scintillation crystals 100 and 120 within a pre-defined time limit. Thus, the gamma ray timing detection system detects gamma rays simultaneously at scintillation crystals 100 and 120. However, for simplicity only, gamma ray detection is described relative to scintillation crystal 100.

One of ordinary skill in the art will recognize, however, that the description given herein with respect to scintillation crystal 100 is equally applicable to gamma ray detection at scintillation crystal 120.

Each photomultiplier tube 110, 135, 140 and 195 is respectively connected to data acquisition unit 150. The data acquisition unit 150 includes hardware configured to process the signals from the photomultiplier tubes. The data acquisition unit 150 measures the arrival time of the gamma ray. The data acquisition unit 150 produces two outputs (one for the combination of PMT 135/140 and one for the combination of PMT 110/195) which encodes the time of the discriminator pulse relative to a system clock (not shown). For a time-of-flight PET system, the data acquisition unit 150 typically produces a time stamp with an accuracy of 15 to 25 ps. The data acquisition unit measures the amplitude of the signal on each PMT (four of the outputs from data acquisition unit 150).

The data acquisition unit outputs are provided to a CPU 170 for processing. The processing consists of estimating an energy and position from the data acquisition unit outputs and an arrival time from the time stamps output for each event, and may include the application of many correction steps, based on prior calibrations, to improve the accuracy of the energy, position, and time estimates.

Moreover, the CPU 170 is configured to perform a method for estimating random events according to the flowchart shown in FIG. 4 and described above.

As one of ordinary skill in the art would recognize, the CPU 170 can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog or any other hardware description language and the code may be stored in an electronic memory directly within the FPGA or CPLD, or as a separate electronic memory. Further, the electronic memory may be non-volatile, such as ROM, EPROM, EEPROM or FLASH memory. The electronic memory may also be volatile, such as static or dynamic RAM, and a processor, such as a microcontroller or microprocessor, may be provided to manage the electronic memory as well as the interaction between the FPGA or CPLD and the electronic memory.

Alternatively, the CPU 170 may be implemented as a set of computer-readable instructions stored in any of the above-described electronic memories and/or a hard disc drive, CD, DVD, FLASH drive or any other known storage media. Further, the computer-readable instructions may be provided as a utility application, background daemon, or component of an operating system, or combination thereof, executing in conjunction with a processor, such as a Xeon processor from Intel of America or an Opteron processor from AMD of America and an operating system, such as Microsoft VISTA, UNIX, Solaris, LINUX, Apple, MAC-OS and other operating systems known to those skilled in the art.

Once processed by the CPU 170, the processed signals are stored in electronic storage 180, and/or displayed on display 145. As one of ordinary skill in the art would recognize, electronic storage 180 may be a hard disk drive, CD-ROM drive, DVD drive, FLASH drive, RAM, ROM or any other electronic storage known in the art. Display 145 may be implemented as an LCD display, CRT display, plasma display, OLED, LED or any other display known in the art. As such, the descriptions of the electronic storage 180 and the display 145 provided herein are merely exemplary and in no way limit the scope of the present advancements.

FIG. 5 also includes an interface 175 through which the gamma ray detection system interfaces with other external devices and/or a user. For example, interface 175 may be a USB interface, PCMCIA interface, Ethernet interface or any other interface known in the art. Interface 175 may also be wired or wireless and may include a keyboard and/or mouse or other human interface devices known in the art for interacting with a user.

While certain embodiments have been described, these embodiments have been presented by way of example only, and are not intended to limit the scope of the inventions. Indeed, the novel methods and systems described herein may be embodied in a variety of other forms. Furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A method of estimating random events in positron emission tomography (PET) list mode data for improved reconstruction of a PET image, the method comprising:
    obtaining time-of-flight (TOF) list mode count data that includes TOF information;
    converting the obtained TOF list mode count data into four-dimensional (4D) non-TOF raw sinogram count data, without using the TOF information, wherein the 4D non-TOF raw sinogram count data includes random count values;
    interpolating the 4D non-TOF raw sinogram count data to generate 4D non-TOF interpolated sinogram count data;
    low-pass filtering the 4D non-TOF interpolated sinogram count data to remove noise;
    converting the low-pass filtered 4D non-TOF interpolated sinogram count data into filtered 4D non-TOF raw sinogram count data;
    generating, by a processing circuit, five-dimensional (5D) TOF raw sinogram count data from the filtered 4D non-TOF raw sinogram count data; and
    reconstructing, by the processing circuit, the PET image using the 5D TOF raw sinogram count data.

2. The method of claim 1, wherein the generating step comprises:
    generating the 5D TOF raw sinogram count data $\hat{r}$(rad, phi, slice, t) at each TOF bin t according to the following equation:

$$\hat{r}(rad, phi, \text{slice}, t) = \frac{t_{binsz}}{t_{coin}\cos\theta} r(rad, phi, \text{slice})$$

wherein $t_{coin}$ is a size of a coincidence window in mm, $t_{binsz}$ a TOF bin size in mm, $\hat{r}$(rad, phi, slice) is filtered 4D non-TOF raw sinogram random count data, (rad,phi,slice) are coordinates of a line-of-response (LOR) in the raw sinogram space, and $\theta$ is an oblique angle of the LOR.

3. The method of claim 1, wherein the obtaining step comprises:
    obtaining the TOF list mode data, which for each coincident event, has a format $\{x_a, z_a, x_b, z_b, e_a, e_b, \text{tof}\}$, wherein $x_a$, $x_b$ are incident transverse crystal numbers of events a and b, respectively; $z_a$, $z_b$ are incident axial crystal numbers of events a and b, respectively; and $e_a$, $e_b$ are energy levels of events a and b, respectively, and tof is an arrival time difference of events a and b.

4. The method of claim 1, further comprising:
    estimating the random count values within the 4D non-TOF raw sinogram count data using a delayed coincidence window method.

5. An apparatus for estimating random events in positron emission tomography (PET) list mode data for improved reconstruction of a PET image, the apparatus comprising:
    a memory storing time-of-flight (TOF) list mode count data that includes TOF information; and
    a processor configured to
        convert the stored TOF list mode count data into four-dimensional (4D) non-TOF raw sinogram count data, without using the TOF information, wherein the 4D non-TOF raw sinogram count data includes random count values;
        interpolate the 4D non-TOF raw sinogram count data to generate 4D non-TOF interpolated sinogram count data;
        low-pass filter the 4D non-TOF interpolated sinogram count data to remove noise;
        convert the low-pass filtered 4D non-TOF interpolated sinogram count data into filtered 4D non-TOF raw sinogram count data;
        generate five-dimensional (5D) TOF raw sinogram count data from the filtered 4D non-TOF raw sinogram count data; and
        reconstruct the PET image using the 5D TOF raw sinogram count data.

6. The apparatus of claim 5, wherein the processor is further configured to:
    generate the 5D TOF raw sinogram count data $\hat{r}$(rad, phi, slice, t) at each TOF bin t according to the following equation:

$$\hat{r}(rad, phi, \text{slice}, t) = \frac{t_{binsz}}{t_{coin}\cos\theta} r(rad, phi, \text{slice})$$

wherein $t_{coin}$ is a size of a coincidence window in mm, $t_{binsz}$ is a TOF bin size in mm, $\hat{r}$(rad, phi, slice) is filtered 4D non-TOF raw sinogram random count data, (rad,phi,slice) are coordinates of a line-of-response (LOR) in the raw sinogram space, and $\theta$ is an oblique angle of the LOR.

7. The method of claim 5, wherein the memory stores the TOF list mode data, which for each coincident event, has a format $\{x_a, z_a, x_b, z_b, e_a, e_b, \text{tof}\}$, wherein $x_a$, $x_b$ are incident transverse crystal numbers of events a and b, respectively; $z_a$, $z_b$ are incident axial crystal numbers of events a and b, respectively; and $e_a$, $e_b$ are energy levels of events a and b, respectively, and tof is an arrival time difference of events a and b.

8. The method of claim 5, wherein the processor is further configured to:
    estimate the random count values within the 4D non-TOF raw sinogram count data using a delayed coincidence window method.

* * * * *